United States Patent
Schmidt et al.

(12) 
(10) Patent No.: US 6,841,675 B1
(45) Date of Patent: Jan. 11, 2005

(54) PIPERAZINE-BASED NUCLEIC ACID ANALOGS

(75) Inventors: Jurgen Schmidt, Los Alamos, NM (US); Louis A. Silks, White Rock, NM (US); Ryszard Michalczyk, Santa Fe, NM (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/171,073

(22) Filed: Jun. 13, 2002

(51) Int. Cl.$^7$ .................... C07D 241/00; C07D 241/02; A61K 31/495
(52) U.S. Cl. .................. 544/336; 544/244; 544/358; 514/252.12; 514/34; 536/22.1; 536/26.1; 536/28.1; 536/28.2
(58) Field of Search ................................ 544/244, 336, 544/358; 514/252.12, 34; 536/22.1, 26.1, 28.1, 28.2

(56) References Cited

U.S. PATENT DOCUMENTS 5,861,397 A * 1/1999 Wheeler et al.

FOREIGN PATENT DOCUMENTS

JP 06-247942 * 9/1994

* cited by examiner

*Primary Examiner*—James O. Wilson
*Assistant Examiner*—Traviss C. McIntosh, III
(74) *Attorney, Agent, or Firm*—Madson & Metcalf

(57) ABSTRACT

A novel nucleoside analog is disclosed which comprises a piperazine ring in the place of the ring ribose or deoxyribose sugar. Monomers utilizing a broad variety of nucleobases are disclosed, as well as oligomers comprising the monomers disclosed herein linked by a variety of linkages, including amide, phosphonamide, and sulfonamide linkages. A method of synthesizing the nucleoside analogs is also disclosed.

18 Claims, 15 Drawing Sheets

PIPERAZINE-BASED NUCLEIC ACID ANALOGS

GOVERNMENT RIGHTS

This invention was made with Government support under Contract Number W-7405-ENG-36 awarded by the United States Department of Energy to The Regents of the University of California. The Government has certain rights in the invention.

BACKGROUND OF THE INVENTION

1. Field of the Invention

The present invention relates to the development of monomers of nucleic acid analogs and their oligomers. More specifically, the present invention relates to novel nucleic acid analog monomers and oligomers which use a piperazine ring in place of the ribose or deoxyribose sugar and to methods of synthesizing such monomers and oligomers.

2. Description of Related Art

Nucleotides and nucleosides are important molecules that participate in many vital cellular functions. Nucleotides serve as cellular signaling molecules, carriers of chemical energy, and building blocks of nucleic acids. See Alberts, et al., *Molecular Biology of the Cell*, 3d ed., (1994). Nucleotides also combine with other compounds to form enzymes.

Structurally, nucleotides are composed of a purine or pyrimidine base attached to a ribose or deoxyribose sugar with, in some cases, one or more phosphate groups joined to the sugar by ester linkages. Nucleotides lacking the phosphate groups are called nucleosides. Energy is stored in nucleotides as bond energy by enzymes that attach the phosphate groups to them in a reaction called phosphorylation. These enzymes are commonly known as "kinases," an abbreviation of the term "phosphokinase."

Nucleotides may be found alone as monomers, but are also often found as oligonucleotides-polymeric sequences of nucleotides joined together. Oligonucleotides have been shown to be useful in many applications, including as PCR primers, as probes in DNA cloning, in mutagenesis techniques, and in gene expression. In order to extend the functions of these useful polymers, efforts have been made to construct oligonucleotides using artificial nucleotides or molecules analogous to nucleotides. Such oligonucleotides are often referred to as oligonucleotide analogs.

Oligonucleotide analogs can be configured to bind DNA or RNA in a sequence specific manner. Agrawal, *Antisense Therapeutics*, (1996); de Mesmaeker et al., *Acc. Chem. Res.*, 28:366 (1995); and Nielsen *Adv. DNA Sequence Specific Agents*, 3, 267–278, (1998). Such oligonucleotides are referred to as "antisense" when they are complementary to a sequence of mRNA. Thus when added to a mixture containing the mRNA, they bind to the mRNA, deactivating it. In contrast, they are referred to as "antigene" when they are complementary to the sequence of a gene, and are thus capable of binding to the gene. Such binding generally prevents further transcription of the gene.

Because oligonucleotides and their analogs have such useful functions, they have become the focus of research seeking novel approaches for modulating genetic diseases using drugs. Rhodes and James, *AIDS* 5, 145, (1991); Li et al., *J. Virol.* 76, 6882, (1993); Liesziewicz et al., *Proc. Natl. Acad. Sci. U.S.A.*, 90, 3860, (1993). They have also garnered attention as research tools for use in probing gene function, genomic structure, and RNA folding. Using oligonucleotide analogs as a targetable knock-out tool holds promise for extracting important information from available genetic information. Mologni et al., *Nucleic Acids Res.*, 26(8), 1934–1938, (1998); Good and Nielsen *Nat. Biotechnol.*, 16(4), 355–358, (1998); Good et al., *Nielsen Proc. Natl. Acad. Sci. U.S.A.*, 95(5), 2073–2076, (1998).

Hexose nucleotides and peptide-linked oligonucleotides have become a prime focus of research as possible precursors of RNA/DNA since to date no prebiotic ribose or pentose nucleotide phosphate syntheses have been demonstrated. Pitsch et al., *Helv. Chim. Acta.*, 76(6):2161–2183 (1993); Orgel, *NATO ASI Ser., Ser. A*, 169:215–224 (1989); Bohler, et al., *Nature*, 376(6541):578–581; and Pitsch et al., *Origins Live Evol. Biosphere*, 25(4):297–334 (1995). Aside from this, the instability of DNA/RNA renders it unfit for many medical and research applications that require an information encoding system with greater shelf-stability.

The most commonly used nucleotide analogs include phosphothioates, methylphosphonates, and peptide nucleic acids. Miller et al., Biochemistry, 20:1878 (1981); Heinemann et al., *Nucleic Acids Res.*, 19:42 (1991); Jayaraman et al., *Proc. Natl. Acad. Sci. U.S.A.*, 78:1537 (1981); Wittung et al., *Nature*, 368:561 (1994); Nielsen et al., *Science*, 254:1497 (1991); and Egholm et al., *Nature*, 365:566 (1993). Phosphothioates and methylphosphonates are successfully used in part because they are not subject to the rapid nuclease-mediated biodegradation that renders DNA and RNA unstable. These analogs are generally found as heterochiral mixtures, and are difficult to obtain in an enantiomerically pure form. Stec & Wilk, *Angew. Chem.*, 106:747 (1994). Disadvantages of these analogs include the fact that they are unspecific in their binding to proteins, and that they are often cytotoxic. Sarmiento et al., *Antisense Res. and Develop.*, 2:99 (1994).

Peptide nucleic acids ("PNAs") are another commonly used form of nucleic acid analogs. In structure, PNAs are amide-linked and non-chiral. They have a strong binding affinity to natural oligonucleotides. Nielsen, *Biophys. Chem.*, 68(1–3):103–108 (1997). Another reason for their current widespread use is their ability to be synthesized through peptide solid phase synthesis. Christensen, et al., *J. Pept. Sci.*, 1(3):185–183 (1995).

Newer PNAs have been modified to be chiral, use side chains, improve solubility, induce predictable binding preference for antiparallel double strand orientation, and to influence helical orientation on PNA binding. Still other new conformationally restricted piperidinone PNA adenine monomers have been developed and used in duplex formation. Nielsen et al., *J. Chem. Soc., Perkin Trans.*, 1:2757–2763 (2001).

These currently used nucleotide analogs are limited in use, however, due to several of their inherent properties. First, uncharged linear oligonucleotides decrease in solubility in purine-rich sequences and as they increase in length. Second, their physicochemical properties are often limited by the base composition of the sequence. Third, they exhibit strong tendencies to self-aggregate, and are often characterized by low intracellular bioavailability. Fourth, all commonly-known uncharged nucleotide analogs require delivery through cell and nuclear membranes for antigene use, and require high intracellular concentrations for antisense use. Fifth, most of the known charged nucleotide analogs are incapable of inducing digestion of mRNA by RNAse H, a drug target that is promising in its potential use to regulate mRNA translation by blocking an undesired sequence's expression.

From the foregoing, it will be appreciated that it would be a significant advancement in the art to provide novel nucleic acid analog monomers, their oligomers, and methods for synthesizing them. It would be a further advancement in the art to provide novel nucleic acid analogs that exhibit improved solubility properties. It would be yet a further improvement in the art to provide novel nucleic acid analogs which exhibited less tendency to self-aggregate than those known in the art. Additionally, it would be an improvement in the art to provide nucleic acid analogs with improved in vitro bioavailability and which is usable with simple drug delivery methods. The nucleic acid analogs of the invention present additional functionality beyond complementary base recognition and lead to novel biochemical and biological function. Finally, it would be an improvement in the art to provide nucleic acid analogs with the ability to induce RNAse digestion of mRNA by inducing the action of RNAse H. Such compounds and methods are disclosed herein.

SUMMARY OF THE INVENTION

The present invention has been developed in response to the present state of the art, and in particular, in response to the problems and needs in the art that have not yet been fully solved by currently available nucleic acid analogs. The present invention thus provides novel nucleic acid analogs, and includes analog nucleic acid monomers and oligomers utilizing piperazine as a backbone in the place of the naturally occurring ribose or deoxyribose ring.

The monomers of the instant invention are desirable and suitable for use in preparing the novel oligomers of the instant invention having peptide, phosphonamide, carbamate, and sulfonamide linkages in any combination. Further, since the monomers are derived from amino acids, the monomers and oligomers may comprise a wide variety of molecular core structures and a wide variety of other functional groups, including all of the functional groups found in amino acids and amino acid analogs. Indeed, within the scope of the instant invention, the backbone linkage length could span from about 1 to about 4 carbons (or other atoms such as oxygen, nitrogen, or sulfur) in length from the branching point of the piperazine core, as well as from the corresponding heteroatom links (phosphonamide, phosphoramidate; sulfonamide, and amide).

Many variations are possible within the scope of the instant invention, including variants built using a combination of any suitable pair of known amino acids and/or amino acid analogs and their stereoisomers. In addition, oligonucleotides may be created within the scope of the instant invention that include any combination of the monomers of the instant invention and natural or synthetic DNA or RNA or other nucleoside analogs. These monomers and oligomers may also be used to generate large chemical libraries using techniques known in the art.

The amino acid-derived sidechain functionality denoted $R^2$ and $R^3$ in the figure of the piperazine is unique and novel. This region of the molecule will likely provide useful biological and medicinal applications beyond antisense nucleobase/nucleobase interactions and hydrogen bonding. In some embodiments of the instant invention, nucleoside analogs represented by the following formula are included:

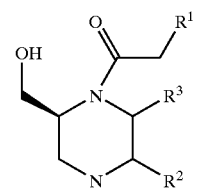

The figure shows the schematic representation of the embodiment with $R^1$ selected from the group consisting of adenine, thymine, uracil, guanine and cystosine. $R^2$ and $R^3$ are side chain groups derived from amino acids and amino acid analogs, or any diastereoisomeric combinations thereof. As such, $R^2$ and $R^3$ may be selected from the group consisting of hydrogen and/or all sidechains occurring in the 20 natural amino acids in all isomeric and diastereoisomeric forms and derivatives thereof, such as, but not limited to Serine=$CH_2OH$, and Lys=$(CH_2)_4NH_2$. In other embodiments, the nucleobase is a nucleobase derivative selected from the group consisting of inosine, fluorouracil, and allyluracil. The nucleobase may further be chosen from a group of nucleobase analogs including daunamycin, and other polycyclic or aromatic hydrocarbon residues known to bind to DNA/RNA.

In many of these embodiments, the piperazine nucleic acid analogs may be so configured as to be capable of forming a phosphoramidite, sulfonamide, or carbonylamide backbone linkage. They may also generally be rapidly assembled in a few synthetic steps from commercial grade materials. The length of the linkage between piperazine rings in the nucleic acid analogs of the instant invention may vary from one to four carbons in length, and may be branched or unbranched. The nucleic acid analogs of the instant invention are also compatible with standard solid phase synthesizers, and may thus be used with synthesizers currently used in the art to allow easy assembly of molecules containing them.

As such, some embodiments of the invention comprise the monomers of the instant invention as related above, but altered using means similar to those currently known and practiced in the art to form protected monomers suitable for use in solid phase synthesis and solution phase condensation. In some such embodiments, the nucleoside analog monomer is generally represented by the formula:

wherein R1 is selected from the group consisting of adenine, thymine, cytosine, uracil, and guanine; wherein R2 is selected from the group consisting of:

and

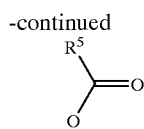

$R^1$ and $R^2$ of the subgroup R2 are selected from a group of phosphonate- and phosphoramide-protecting and activating groups consisting of hydroxy, cyanoethyl, methoxy, benzyl, tert. Butyl, diisopropylamine and/or chloro. $R^3$ is selected from a group consisting of hydroxyl, chloro, hydroxysucciminidyl, pentafluorophenoxy and other groups commonly used in peptide syntheses for the activation of carboxylic acids. $R^4$ is selected from chloro, bromo and other suitable activation groups or amido- and hydroxy- for termination of a nucleoside strand. $R^5$ is selected from a number of commonly used carbonate and carbamate functionalities as chloro-, hydroxy- and nitrophenyloxy- groups.

The subgroup R3 is selected from the group consisting of monomethoxytrityl (MMT), dimethoxy-trityl (DMT), 9-fluorenylmethoxycarbonyl (Fmoc) and tert.-butyloxycarbonyl (Boc). MMT, Fmoc, and Boc are only examples of several other suitable implementations with similar protecting schemes commonly used in solid phase peptide and DNA syntheses.

The invention further comprises amide-, phosphonamide-, carbamate-, and sulphonamide-linked oligomers made up of homo-oligonucleotides or comprising a chimera of either DNA or RNA and the nucleoside analogs of the instant invention. In some embodiments, the oligomer is a composition containing a number, n, of nucleoside monomers represented by the formula:

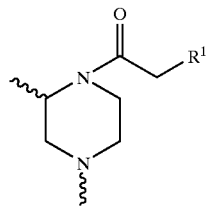

wherein $R^1$ is a nucleobase selected from the group consisting of adenine, thymine, uracil, guanine, and cytosine; wherein n is from about 1 to about 1000; and wherein the nucleoside monomers are joined by amide-, phosphonamide-, carbamate-, or sulfonamide-linkages. In some of these embodiments, R1 may be a nucleobase derivative selected from the group consisting of inosine, fluorouracil, and allyluracil. In others, the nucleobase derivative is chosen from a group including daunamycin and other polycyclic or aromatic hydrocarbon residues known to bind to DNA/RNA. In some of these oligonucleotide compositions n is from about 1 to about 30. In others, n is from about 30 to about 100. In still others, n is from about 100 to about 1000. The invention further includes oligomers containing branching from the sidechains of the amino acids, rings of oligomers and other tertiary, non-linear structures.

As previously noted, in some of these oligonucleotide compositions, phosphodiester linkages join the monomers. In some of these, the phosphodiester bonds comprise a linker of between about 1 and about 4 carbons in length. In others the monomers are joined by peptide bonds. In some of these, the peptide bonds comprise a linker of between about 1 and about 4 carbons in length. Finally, in other embodiments, sulfonamide bonds join the monomers. In some of these, the sulfonamide bonds comprise a linker of between about 1 and about 4 carbons in length. In other embodiments, carbamate linkages join the monomers. In some of these, the carbamate bonds consist of a linker of between 1 to 4 carbons in length. Included are also all possible chimeric linkages of the possible structures.

These and other features of the present invention will become apparent upon reference to the accompanying figures, upon reading the following detailed description and appended claims, and may be learned by the practice of the invention as set forth hereinafter.

BRIEF DESCRIPTION OF THE DRAWINGS

In order that the manner in which the above-recited and other advantages and objects of the invention are obtained will be readily understood, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

The presently preferred embodiments of the present invention will be best understood by reference to the drawings, wherein like components or structures are designated by like numerals throughout. It will be readily understood that the components of the present invention, as generally described and illustrated in the figures herein, could be arranged and designed in a wide variety of different configurations. Thus, the following more detailed description of the embodiments of the apparatus, system, and method of the present invention, as represented in FIGS. 1 through 13, is not intended to limit the scope of the invention, as claimed, but is merely representative of presently preferred embodiments of the invention.

The present invention relates to piperazine nucleotide and nucleoside analogs in which the piperazine core is used to substitute for the ring ribose sugar in nucleosides. These novel nucleotides exhibit advantages of greater stability, improved solubility, and less tendency to self-aggregate than other nucleic acid analogs currently known and taught in the art. In addition, the nucleic acid analogs of the invention may exhibit improved in vitro bioavailability, and are likely to be administrable through drug delivery methods practiced currently in the art with oligonucleotides analogs. Further, these analogs may be used to induce RNAse H digestion of mRNA. The invention may be better understood by reference to the appended figures. A discussion of these figures follows.

Figure 1:
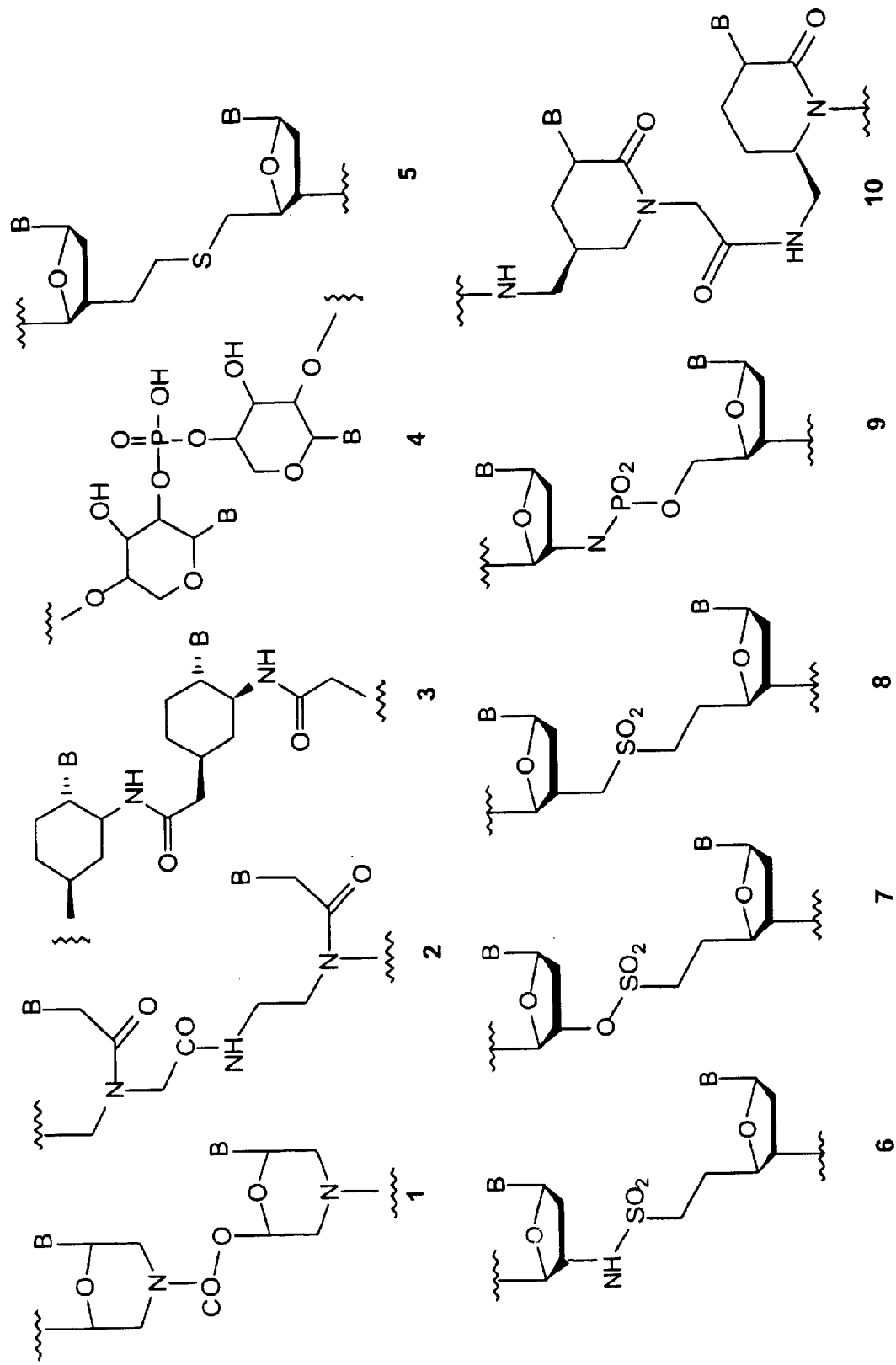
FIG. 1 is a view of the chemical structures of several representative oligonucleic acid analogs.

In FIG. 1, a group of currently known oligonucleic acid analogs is shown. The first is a morpholino analog. These analogs have been shown in bioassays to be biologically well-tolerated if integrated into chimeric sequences in natural DNA/RNA. Bellon et al., *J. Am. Chem. Soc.* 118:3771 (1996). Morpholino analogs are derivatives of RNA obtained in a one-step modification, and are used extensively in modification of RNA and RNA-terminated DNA. Morpholino derived analogs, however, exhibit decreased affinity to complementary strands.

The second example shown is a peptic nucleoside analog, or "PNA." A set of PNAs have been commercialized and made available through perseptive biosystems/Applied biosystems (Foster city, Calif.). Some embodiments of these piperazine analogs of the instant invention are acetyl-linked in a manner similar to PNAs. The third example shown is a cyclohexyl analog. The fourth is a pyranose analog. The fifth is a sulfide analog. The sixth is a sulfonamide analog. The seventh is a sulfolan analog. The eighth is a sulfon analog. The ninth is a phosphoramidate analog. It is useful to note that in addition to the common phosphate linkages very often seen, sulfonamidate and dimethylsulfon linkages are also seen. Structure 10 is a piperidinone PNA as described in Nielsen et al., *J. Chem. Soc., Perkin Trans.*, 1:2757–2763 (2001). Each of these has a structure with elements similar to that of the piperazine-based analogs of the instant invention.

Piperazines are often used in pharmaceutical and medicinal applications, and are widely regarded as being biocompatible, and having very low toxicity. They are commonly used in bisphenyl(aryl)piperazine derivatives as reverse transcriptase inhibitors. FIG. 2A displays the structure of indinavir, a HIV protease inhibitor containing the piperazine core used as a peptide mimic. FIG. 2B further shows a ketopiperazine monomer for use in combinatorial chemistry and peptide mimics. Finally, FIG. 2C shows the GMP analog Viagra™, a well-known impotence drug that uses a terminal piperazine as a scaffold. These known molecules, as with most of those in the prior art, use the piperazine motif largely as a carrier of positive charge under physiological conditions, as a peptidomimic, and as a terminal filler.

Figure 3:
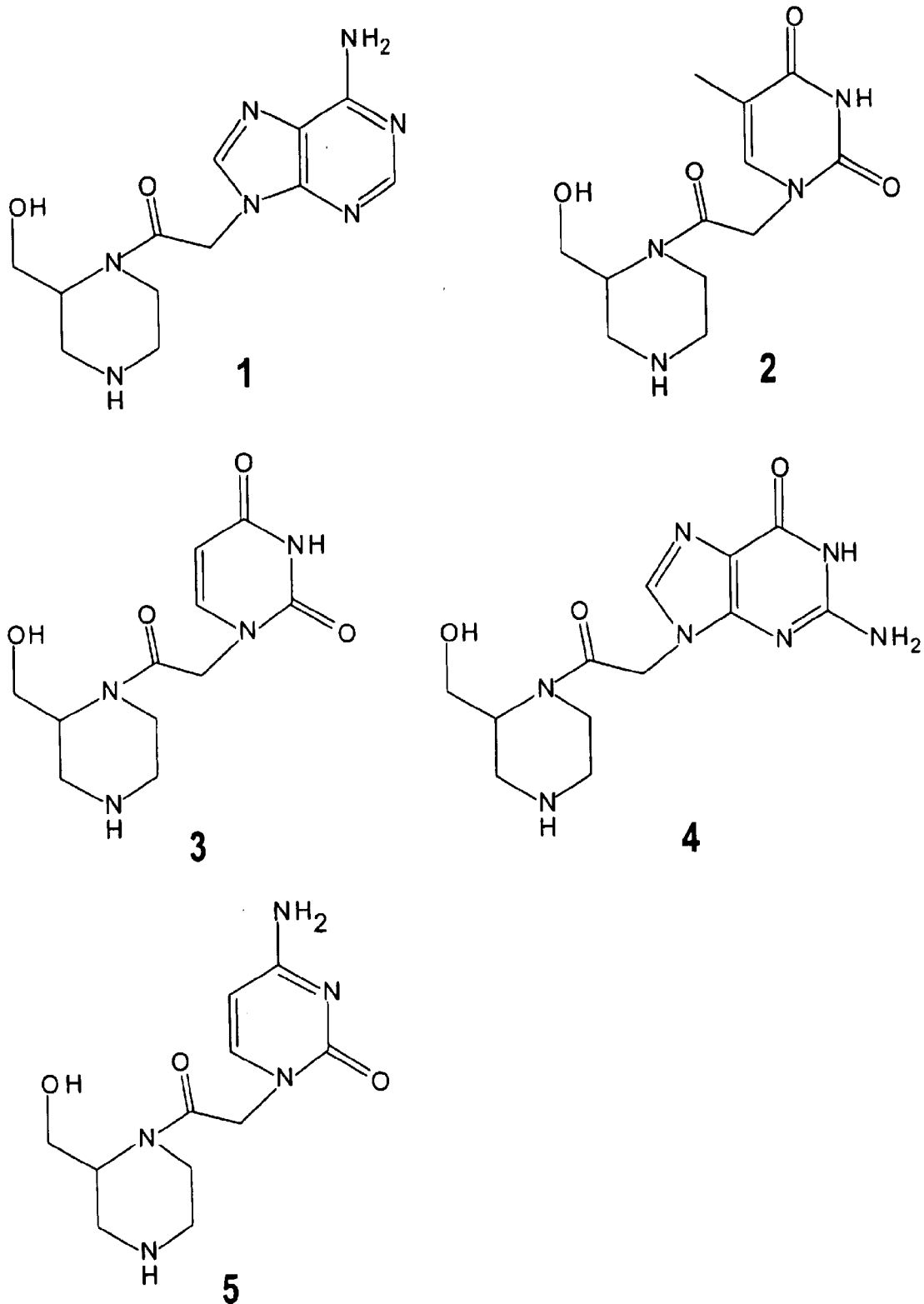
FIG. 3 shows a representation of the nucleic acid analogs of the invention.

Referring now to FIG. 3, the structures of five piperazine-based nucleic acid analog monomers of the instant invention are shown, including: (1) adenine, (2) thymine, (3) uracil, (4) guanine, and (5) cytosine. These analogs are drawn isostructurally to their natural DNA and RNA counterparts. Other examples could be shown, including nucleobase derivatives such as inosine, fluorouracil, allyluracil, or other chemical entities which are suitable for hydrogen bonding to a complementary motif. Other chemicals, including polycyclic or aromatic residues known to bind DNA/RNA, such as daunamycin, may also be used.

Figure 4:
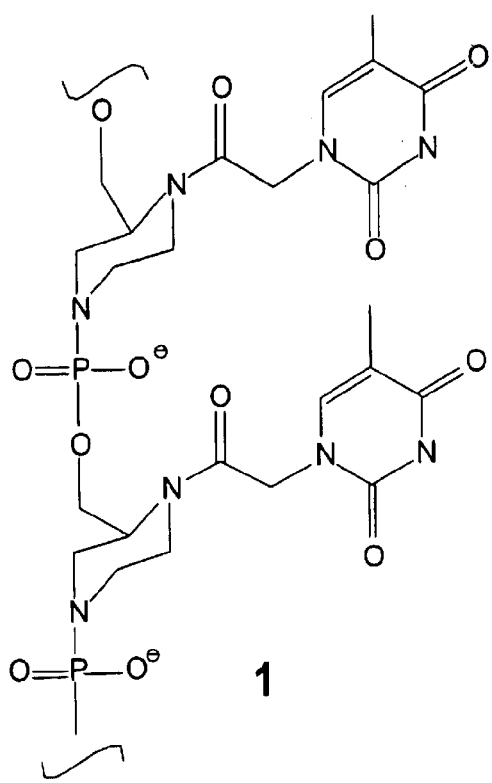
FIG. 4 shows the structure of piperazine and ketopiperazine thymidine oligonucleic acid analogs as phosphoramidites, amides, carbamates, and "uncharged" sulfonamides drawn isostructurally to DNA/RNA.
Figure 4:
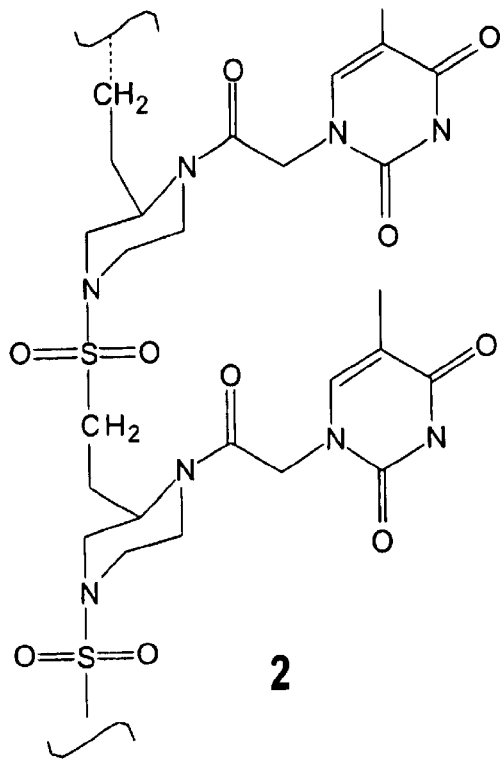
Figure 4:
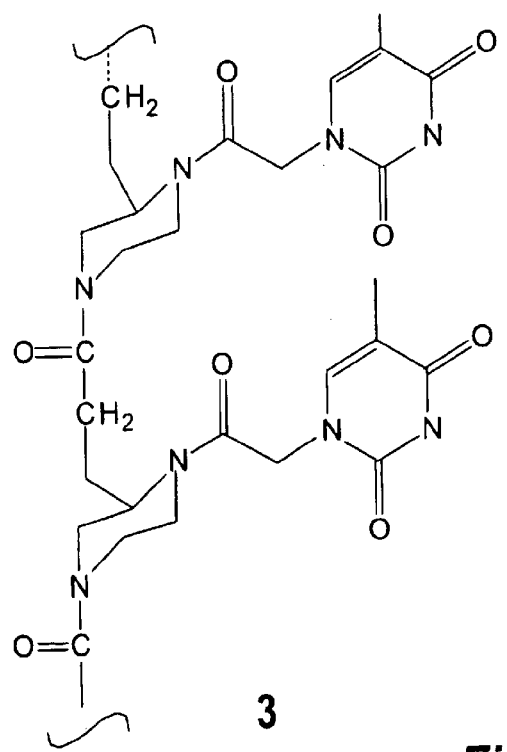
Figure 4:
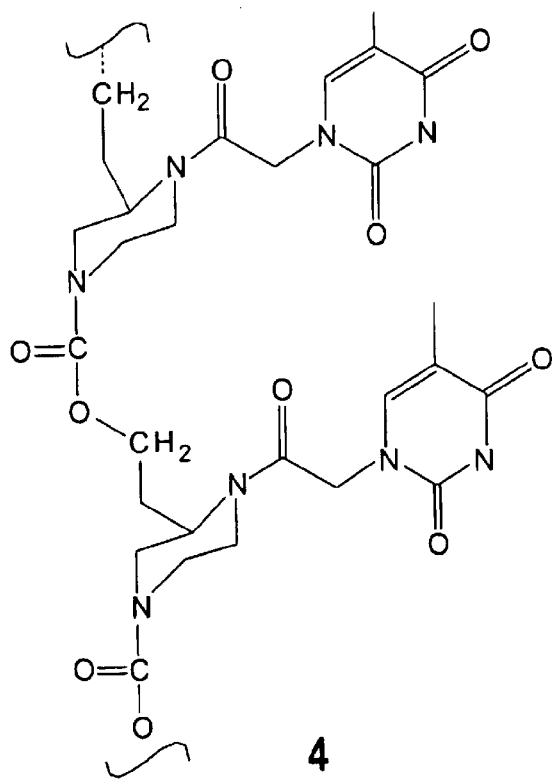

FIG. 4 contains structural diagrams for thymidine piperazine-based analogs drawn isostructurally to DNA/RNA. The diagrams are drawn to show these molecules as phosphonamidates, uncharged sulfonamides, amide-linked structures, and carbamates.

Figure 5:
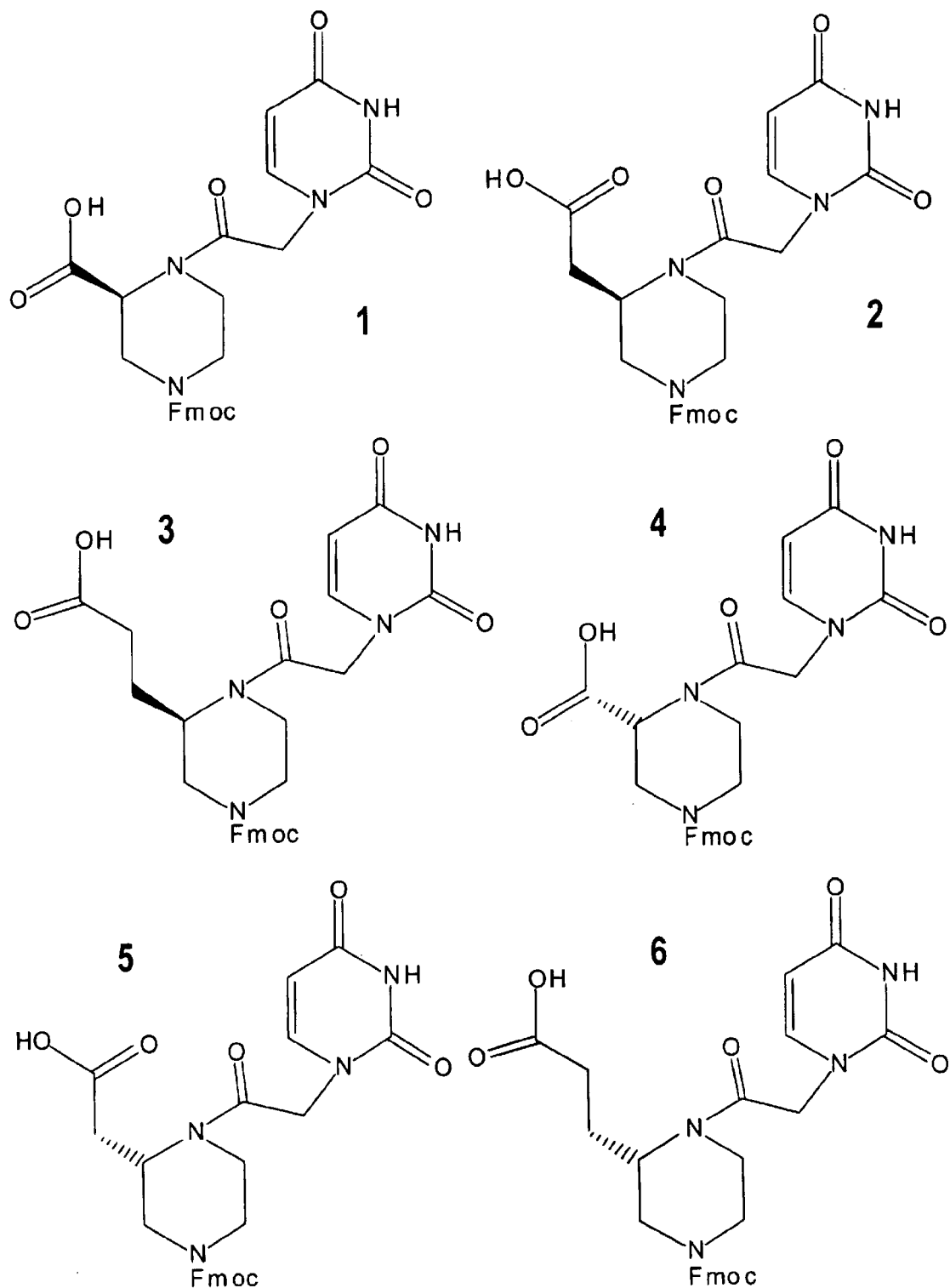
FIG. 5 shows several of the variations of stereochemistry and linker length of compounds of the instant invention.

Referring now to FIG. 5, examples of the stereochemistry and linker length of peptide building blocks of the instant invention are shown. Here, uracil is used as an example with the understanding that the structure of other nucleobases can be ascertained by substituting adenine, guanine, cytosine, or thymidine in the place of uracil. Here, the stereochemistry of the sidechain is not shown since both stereoisomers can be obtained selectively using appropriate amino acid precursors. Indeed, this structure merely exemplifies the peptide building blocks of the instant information, and phosphoramidites and sulfonamide building blocks with linker sizes of 1–4 in carbon length are implicit by analogy.

Figure 6:
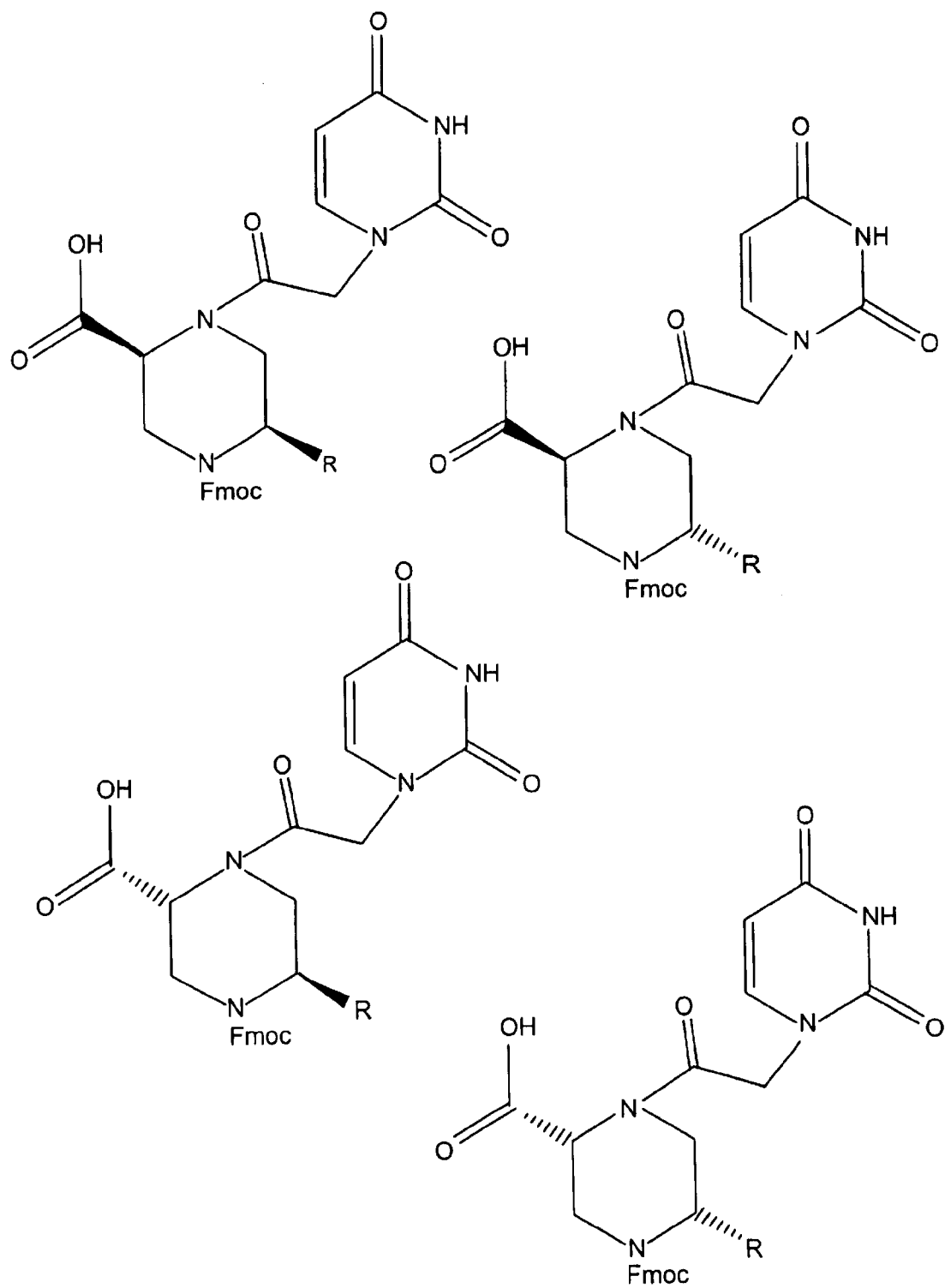
FIG. 6 is an example of a diastereomeric pair of isomers of compounds of the instant invention.
Figure 7A:
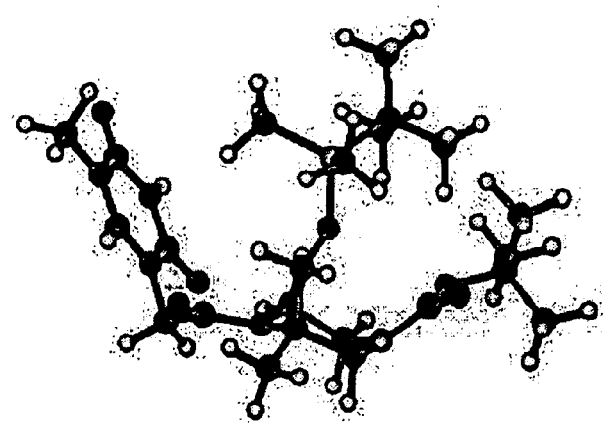
FIG. 7A shows NMR data-assisted molecular modeling of the structure of a deoxythymidine piperazine analog of the instant invention.
Figure 7A:
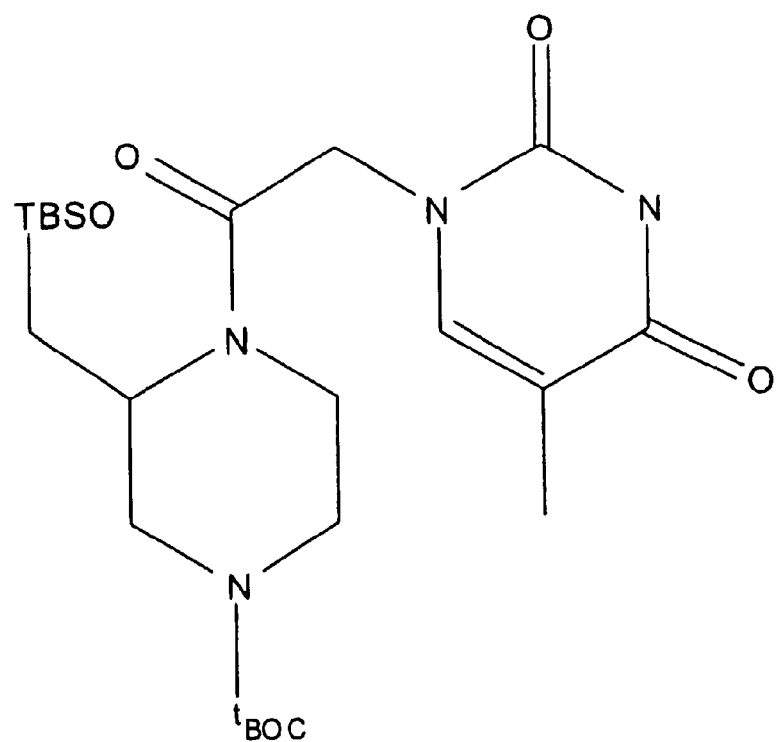
Figure 7B:
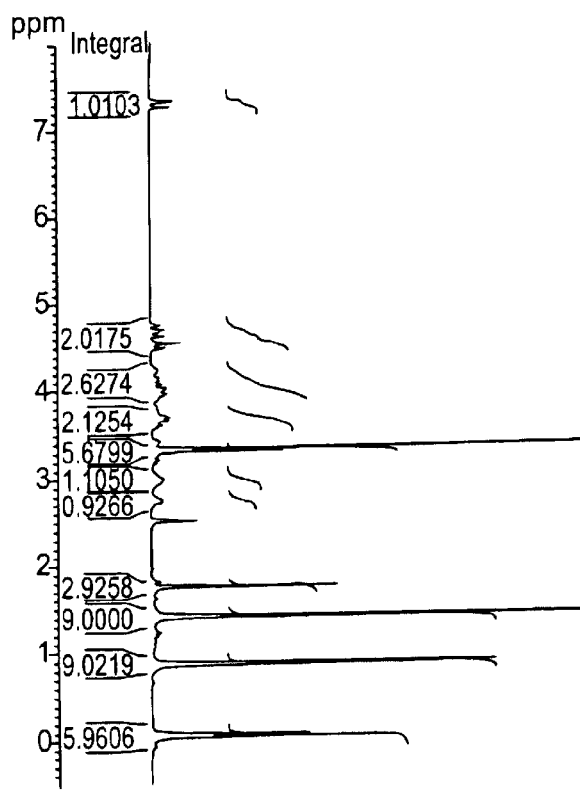
FIG. 7B shows NMR data of the structure of a deoxythymidine piperazine analog of the instant invention.
Figure 7C:
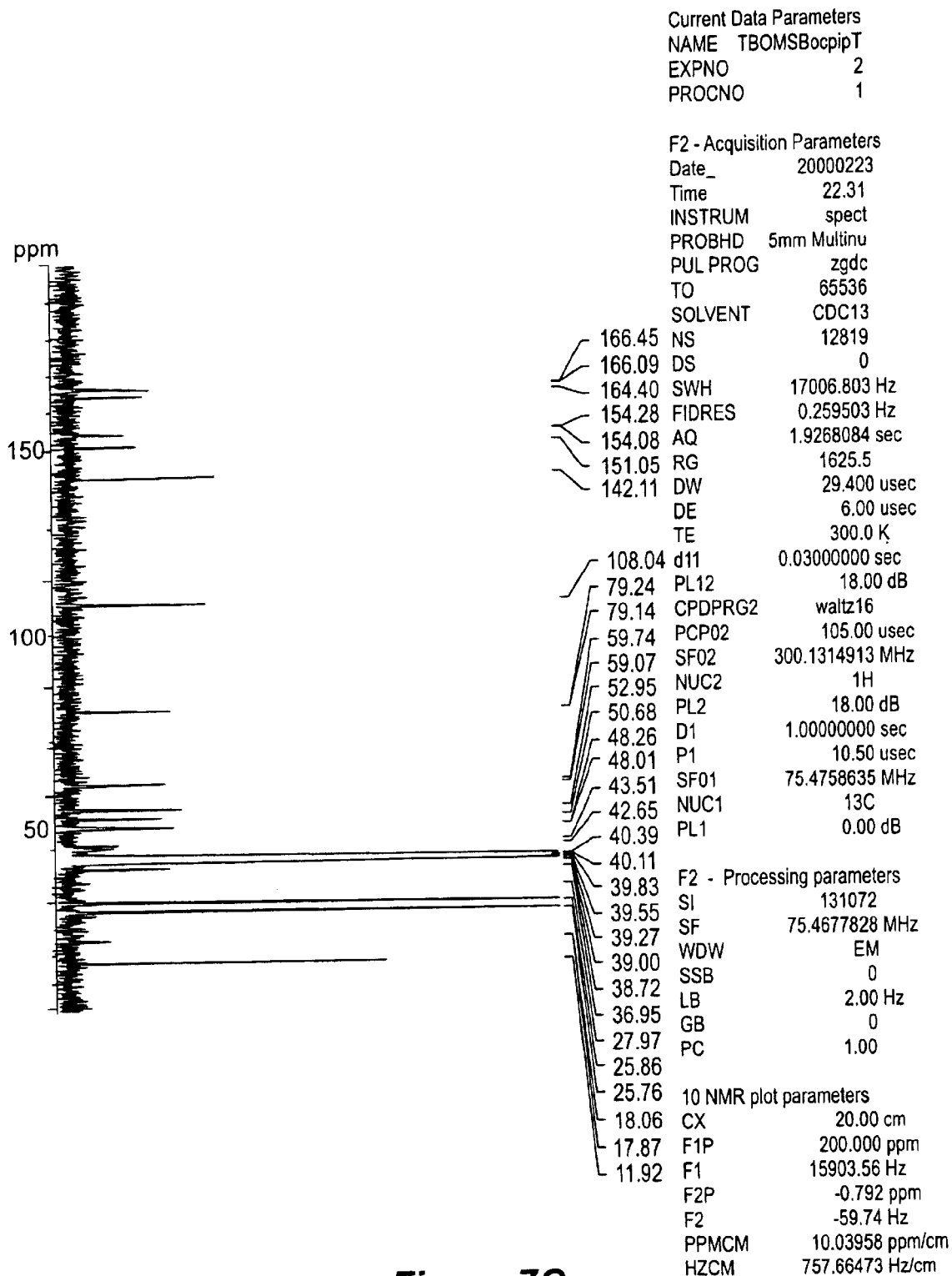
FIG. 7C shows NMR data of the structure of a deoxythymidine piperazine analog of the instant invention.
Figure 8:
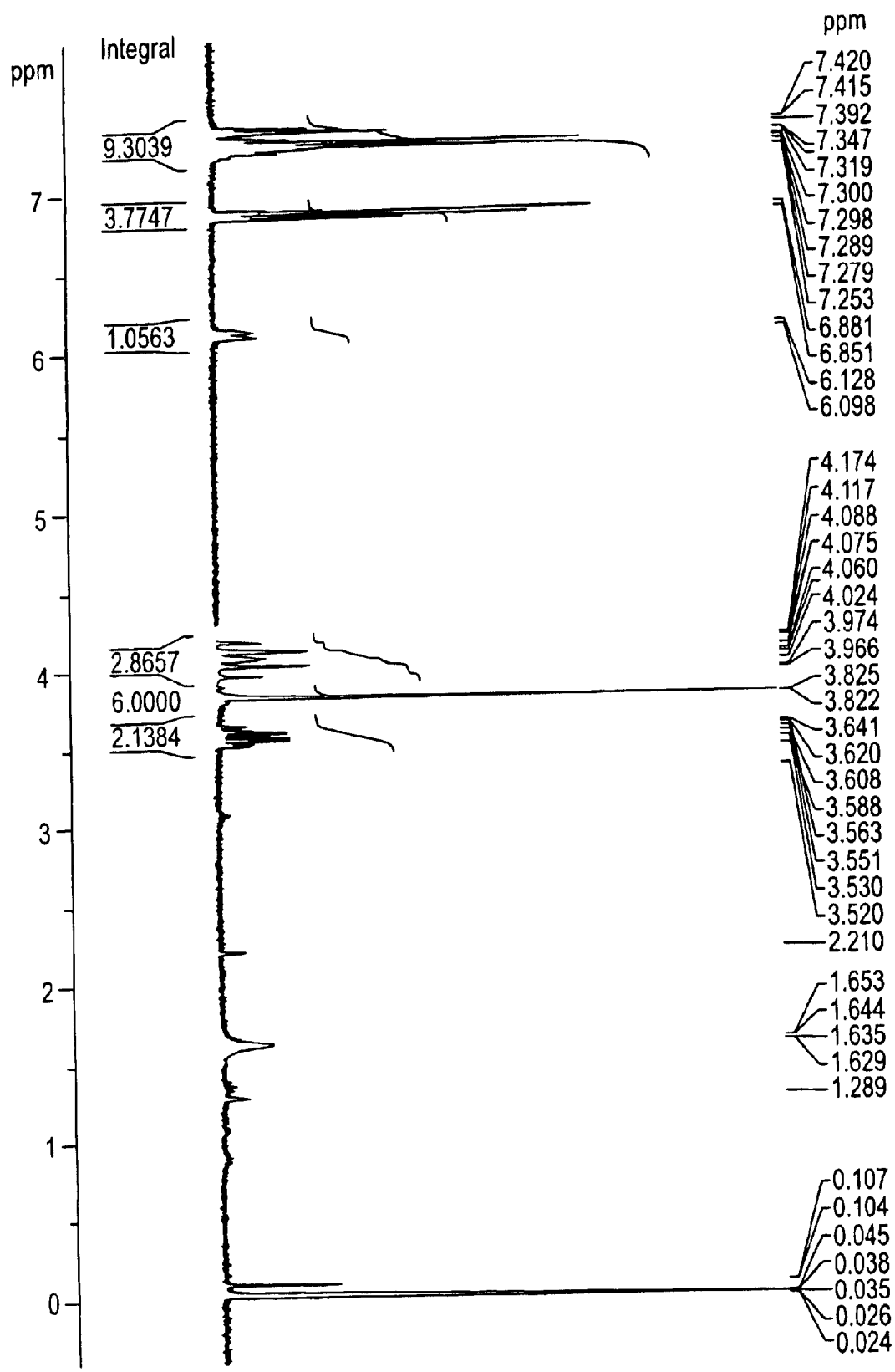
FIG. 8 is a proton NMR spectrum of a serine/glycine monomer intermediate.

FIG. 6 shows an example of a diastereomeric pair of isomers of the piperazine-based nucleic acid analog monomers of the instant invention. FIG. 7A shows the NMR-data-assisted molecular modeling structure of a piperazine-based deoxythymidine nucleoside analog of the instant invention. FIGS. 7B and 7C show NMR data of the structure of a deoxythymidine piperazine analog of the instant invention. FIG. 8 shows a proton NMR spectrum of a Serine/Glycine monomer intermediate of the instant invention.

Figure 2:
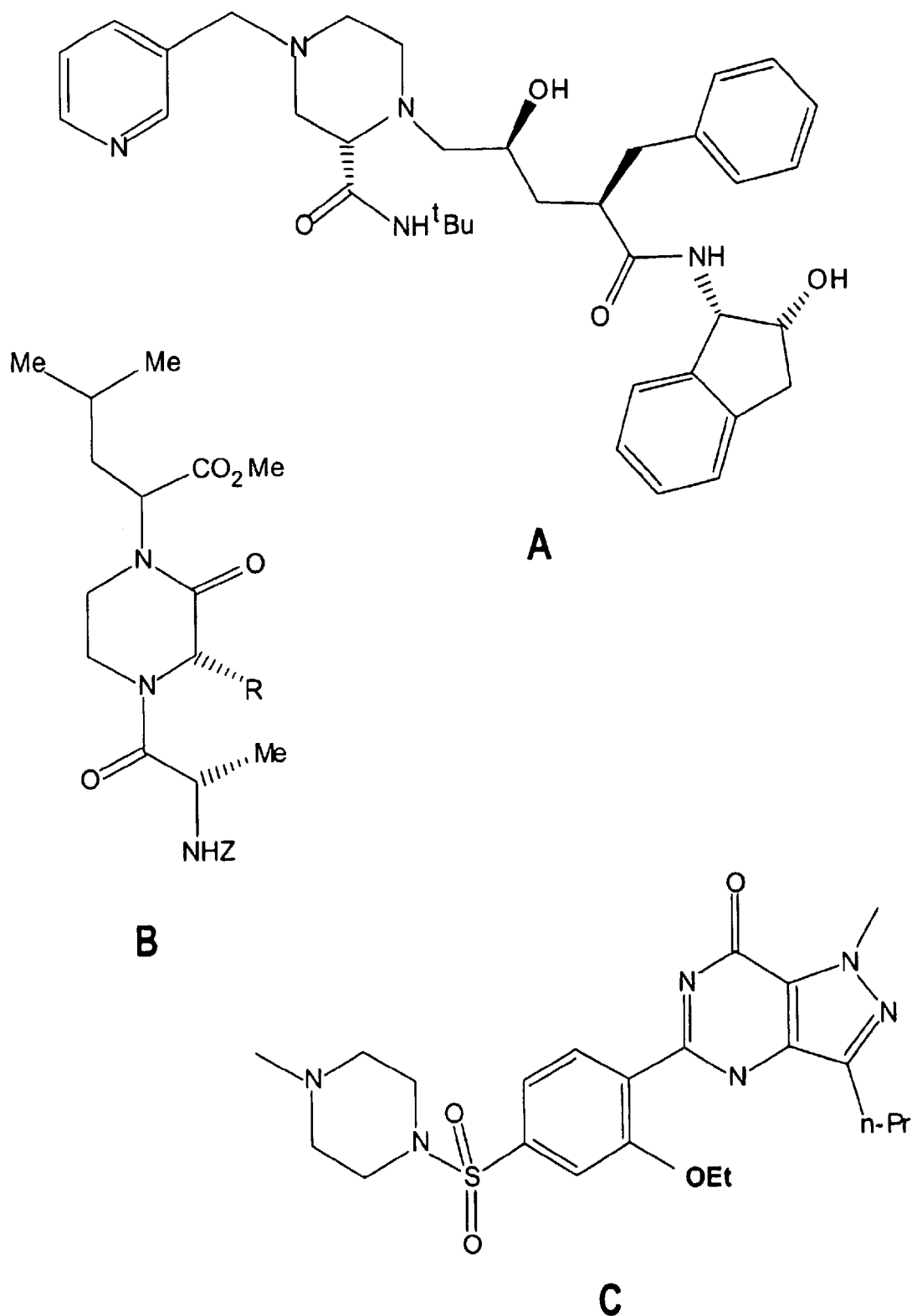
FIG. 2 is a view of the chemical structures of several piperazine and ketopiperazine-based compounds currently known and practiced in the art.
Figure 9:
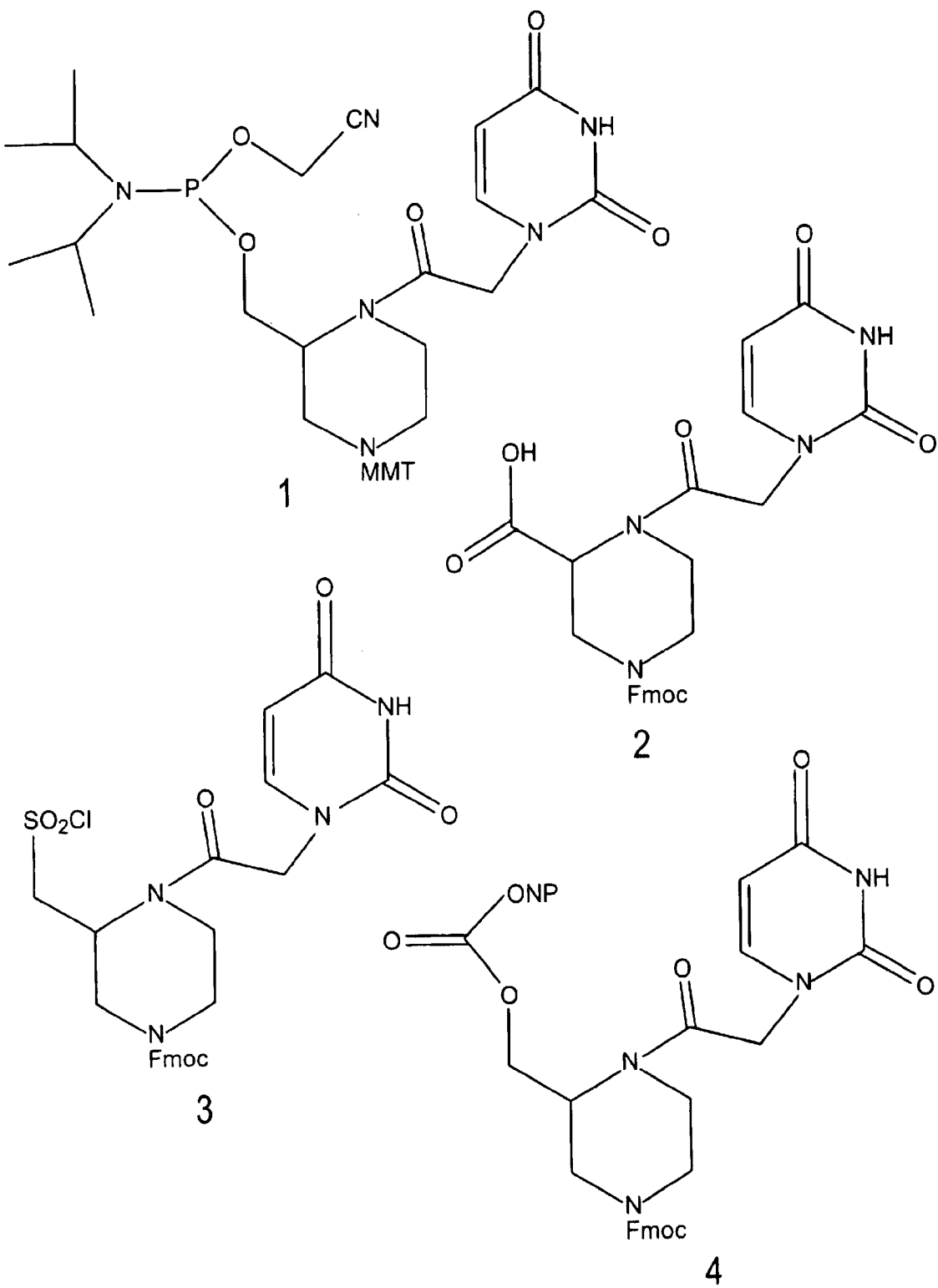
FIG. 9 illustrates the structures of several piperazine nucleoside analogs suitably activated for solid phase syntheses and solution phase condensation to oligomers.

Referring now to FIG. 9, four piperazine-based nucleosides are shown, each being suitably activated for use in solid phase syntheses. FIG. 9-1 shows a MMT-phosphoramidite analog DNA ready for use in a synthesizer. FIG. 9-2 shows a Fmoc-carboxyl-peptide ready for use in synthesis. FIG. 9-3 shows a sulfonamide building block. t-Boc analogs are comparable to Fmoc piperazines substituting t-Boc for Fmoc. Further, the protecting schemes for nucleobases other than uracil shown in the figure are suitable entities commonly used in DNA and peptide syntheses, and are only minimally adjusted to show their respective coupling conditions (such as MMT instead of DMT used in DNA synthesis). FIG. 9-4 shows a carbamate building block. Specifically, FIG. 9-4 shows nitrophenylcarbonate, an activation group that forms a carbamate on coupling with the ring nitrogen of another piperazine monomer to form nucleic acid oligomers.

Figure 10:
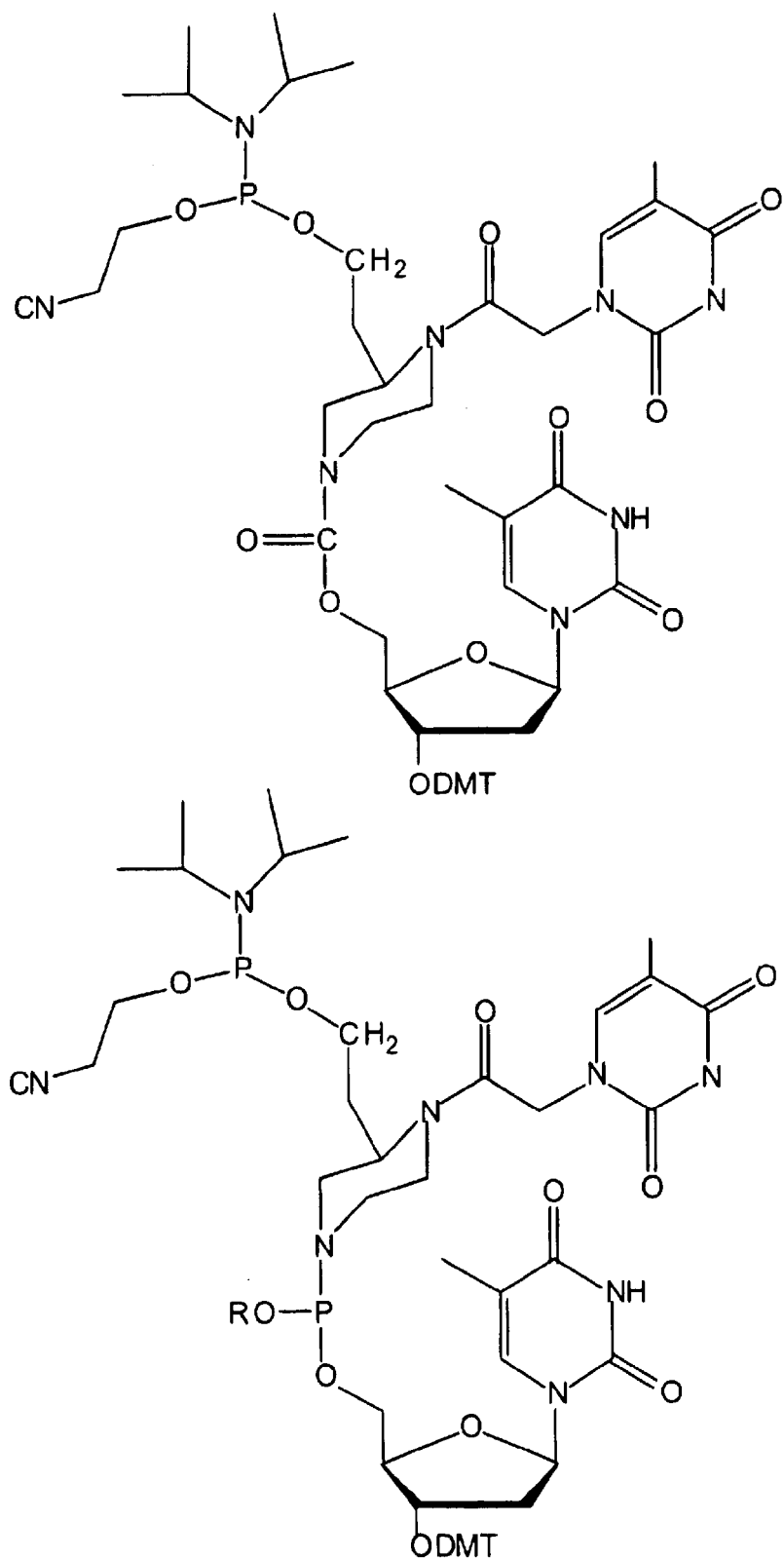
FIG. 10 shows chimeric oligonucleotide analogs of thymidine and its piperazine analog, here shown ready to be used by standard oligonucleotide synthesizers.

FIG. 10 shows chimeras of DNA thymidine with the piperazine-based thymidine analog for automated, standard DNA synthesis. These chimeras are shown prepared for use by standard oligonucleotides synthesizers using DMT-phosphoramidite chemistry.

Figure 11:
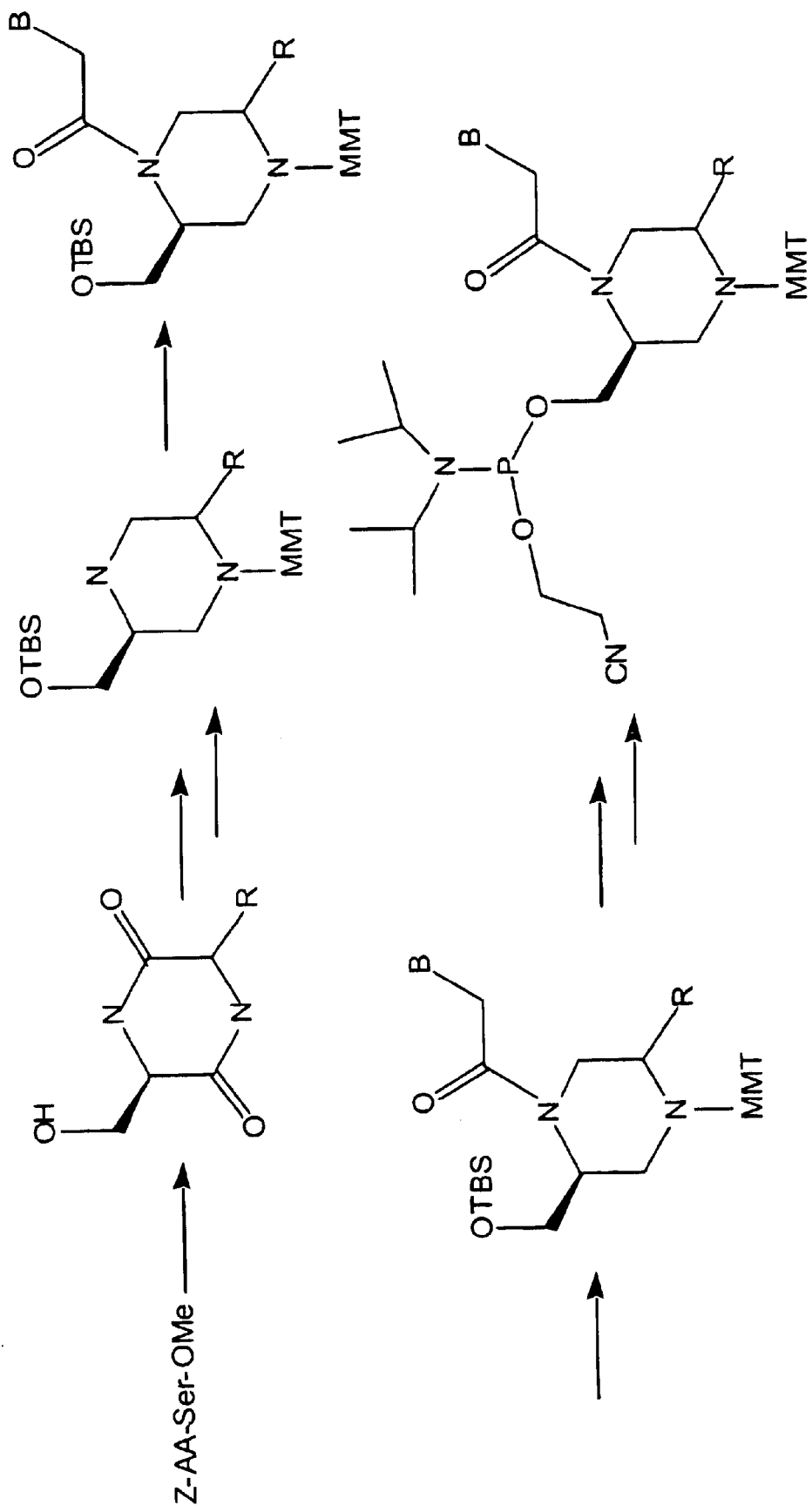
FIG. 11 is a synthetic scheme for the synthesis of piperazine nucleoside building blocks prepared for automated synthesis.

FIG. 11 portrays the general synthetic scheme for the synthesis of piperazine-based building blocks in a state ready for use in automated synthesis. In this figure, AA generically denotes any amino acid, and R corresponds to any amino acid sidechain. In this figure, the phosphoramidite's preferred attachment at the hydroxyl, rather than to the amine, is shown.

Figure 12:
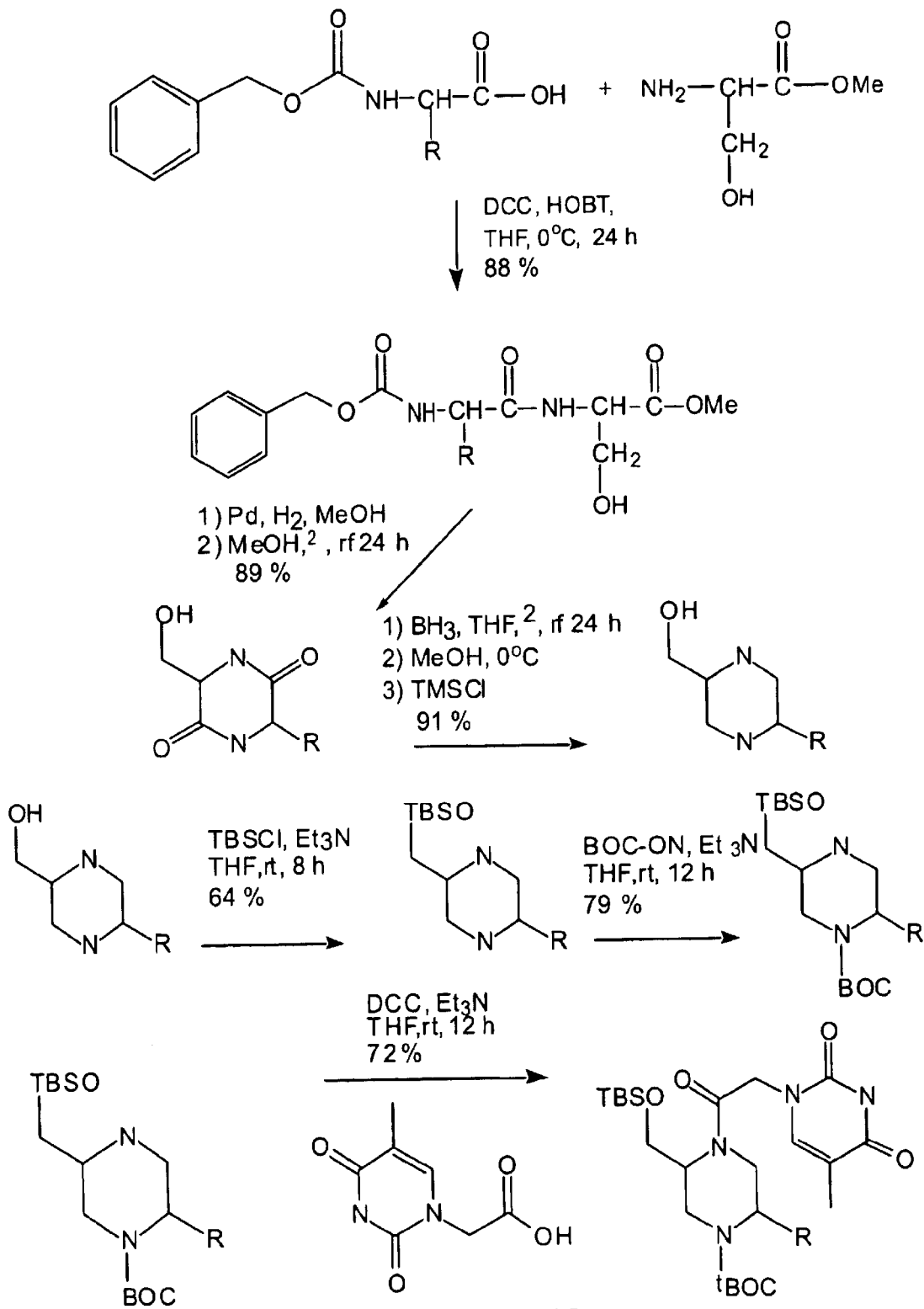
FIG. 12 is the synthetic route used for the syntheses of piperazine nucleoside building blocks.

FIG. 12 shows more specifically the synthetic route used in the syntheses of piperazine nucleoside building blocks. Following this synthetic route leads to the compound whose NMR data are included in FIG. 7.

Figure 13:
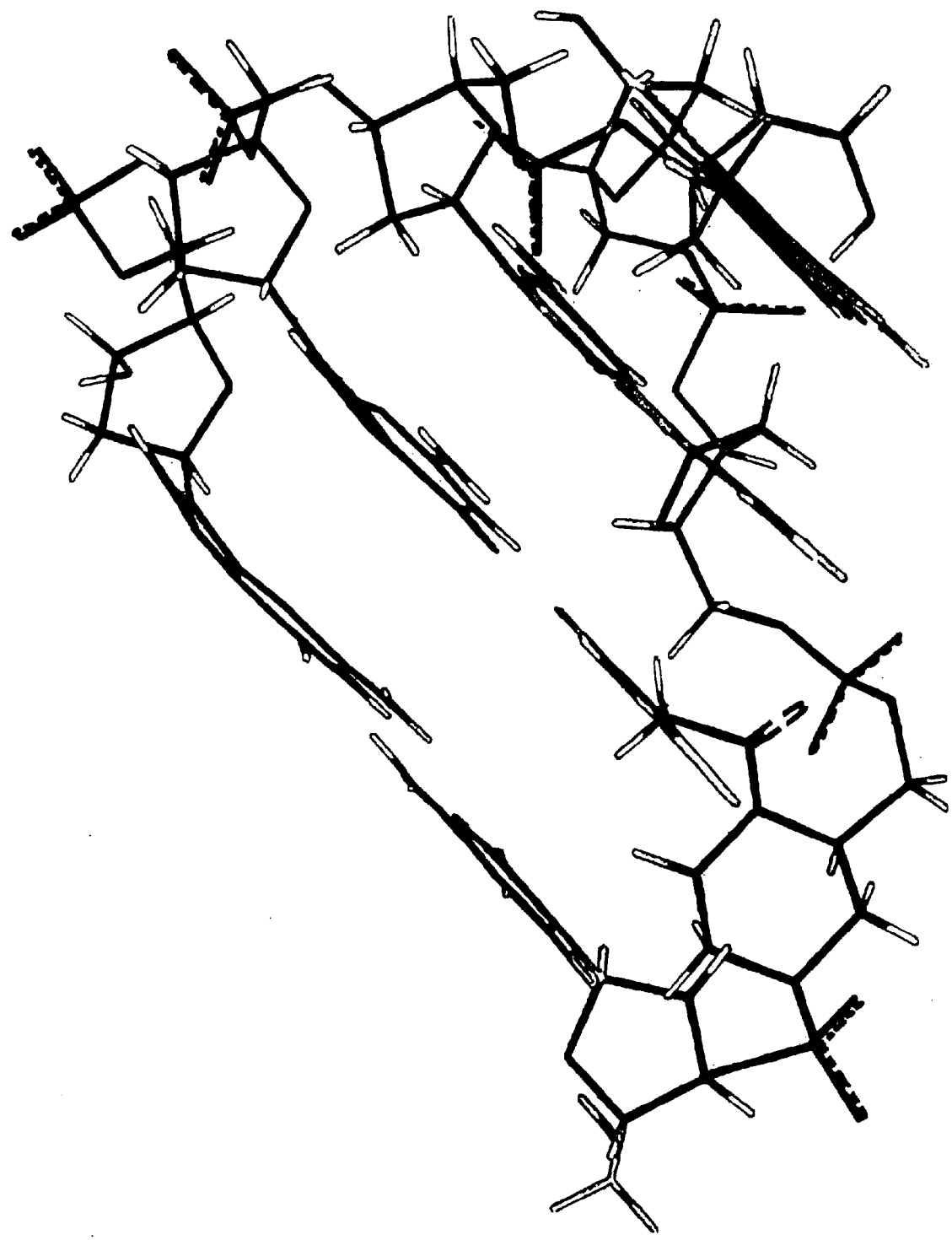
FIG. 13 shows the result of a molecular modeling study, showing one piperazine analog in a chimeric $(GC)_2$—GC (PipG)C duplex.

FIG. 13 shows one exemplary structure of an oligonucleotide containing a piperazine nucleoside analog, obtained in molecular modeling studies. These studies were conducted using Insight II™ by Biosym, Inc. The structures obtained, including the one shown, demonstrate that the nucleoside analogs are capable of Watson-Crick duplex formation with complementary DNA and RNA strands. Further structural studies indicated that the piperazine and ketopiperazine oligonucleotides are isostructural substitutions for DNA. As a result of this, they will not likely inhibit the activation of RNAse H for the digestion of mRNA. Further, due to their structure, the monomers as triphosphates and sulfonamides fit into the binding site of enzymes such as polymerases, kinases, and reverse transcriptase. This ability renders them suitable candidates for use as enzyme inhibitors.

The invention of the instant application in part describes a new approach to the development of oligomeric nucleic acid analogs that uses a novel piperazine scaffold. The target nucleic acid phosphoramidite ready monomers of the invention can be rapidly assembled in as few as three synthetic steps from commercial diketopiperazine starting materials. Construction of the monomers from other heteroatoms or with stable isotopes is accomplished in as few as seven steps. A major advantage of the proposed monomers is that they are compatible with standard oligonucleotide or peptide synthesizers. Molecular modeling studies and comparisons to other oligomeric nucleic acid analogs create the anticipation that stable Watson-Crick base pairing and helical chimeric double strand conformation will be observed. Solution structure characterization of the analogs will increase the potential uses of these oligomeric nucleic acid analogs to include applications as biomolecular tools in antisense and antigene applications. It would further facilitate the evaluation of stability toward enzymatic degradations.

The analogs of the instant invention most closely compare to morpholino nucleic acids analogs. Morpholino analogs can be used to construct Watson-Crick base-paired, information-encoding oligomers that can be used for antisense, antigene, and triple helix binding. Further, the invention of the instant application is suitable for the creation of the discussed backbone linkage on a standard DNA or peptide synthesizer in high yields and gives hydrolytically stable oligomers. (Compare to sulfonamide (6) and phosphoramidate (9) in FIG. 1).

As illustrated in FIG. 4, this observation suggested that incorporating the amines into the heterocycle piperazine as "backbone" would lead to oligomers that perfectly mimic the structural features of natural oligonucleotides, while lowering their tendency toward intramolecular assisted hydrolysis. The core structure of the oligonucleotide acid analogs of the instant application is the piperazine heterocycle. As briefly discussed above, the structure of these analogs and can best be compared to morpholino oligonucleotides. These have been shown in bioassays to be structurally and biologically well tolerated if incorporated within chimeric sequences in natural DNA/RNA.

The monomers of the instant invention appear suitable for use with several linkage types, including amide, phosphoramide, and sulfonamide linkages. Such is the case since where primary phosphoramidates are rapidly hydrolyzed, phosphoramidates of secondary amines are stable to neutral to mild basic pH. Indeed, since the charge density on the phophoramidate-linkage is reduced by P—N conjugation compared to natural phosphodiester linkages, this will lead to high binding affinities for complementary, natural oligonucleotides.

The alternative sulfonamide-, carbamate-, or peptide-(amide-) linkages result in no net charge on the backbone of the oligonucleotide analog. This further avoids the problem of electrostatic repulsion in a double strand to phosphate-linked oligonucleotides and therefore increases the binding affinity to DNA/RNA. The "electro-neutral" backbone modification in the sulfonamide linked analogs makes these molecules more stable towards acid hydrolysis and further offers the possibility of making these compounds lipophilic enough to allow their diffusion through cell membranes. This would likely increase their intracellular bioavailability.

The base in the nucleotide analogs of the instant invention may be attached by an acetyl linker. This flexible linker, known from its use in PNA technologies, compensates for any sub-optimal backbone orientation in an, "isostructural replacement of ribose" by the heterocycle. It further exhibits appreciable stability toward chemical and enzymatic hydrolysis.

In order to ascertain the predicted structure of the oligonucleotides of the instant invention, molecular modeling studies were conducted using Insight II™, by Biosym Inc., on several different template strands. A first of these was run on a piperazine nucleoside in ($GC_4$). The resulting structure obtained from one of these studies is seen in FIG. 13. In summary, these studies indicated that, due to their structure, embodiments of the instant invention are capable of forming duplexes of the "Watson-Crick" type with complementary DNA and RNA strands.

Further molecular modeling studies on target protein structures indicated that piperazine oligonucleotides are isostructural substitutions for DNA and may not inhibit the activation of RNAse H for the digestion of mRNA. These monomers, as triphosphates and sulfonamides, fit into the binding site of polymerases, kinases and reverse transcriptase. They are further suitable to serve as inhibitors of these enzymes.

The structure and composition of these sulfonamide-, amide-, carbamate- and phosphoramidate-linked piperazine oligonucleotide analogs yields the expectation of higher solubility and lower tendency for self-aggregation than other analogs such as corresponding PNA sequences. This combination of physicochemical properties, all of which are necessary for strong antisense binding and for the activation of active uptake mechanisms into cells make this technique appear especially promising for research and therapeutic use.

Further, the substituents of the analogs of the instant invention show promise for use in industry, research and medicine. It is well known and understood that the piperazine core is a common motif in several drugs. As a result of this, the biodegradation of these oligonucleotide analogs will most likely lead to products known to be pharmacologically well tolerated. The sidechain groups constructed by using various amino acids and their analogs introduces additional functionality not found in other oligonucleotides analogs. These structural and functional elements can lead to piperazine oligonucleotides analogs that carry hydrolytical activity towards a complimentary strand, complexing sidechains for the attachment of e.g., radionucleii to these oligomers or branching points for tree- and ring-like oligomeric strands in addition to the linear oligomers shown in the figures.

Chirality is a possibility which has only recently begun to be explored in oligonucleic acid analogs. As an example of this, PNA building blocks have only very recently begun to be constructed from chiral amino acids. It was found that additional functionality was made possible by using, for example, lysine instead of ethylene diamine. This change modified the solubility of the product PNA.

Most of the work conducted on chiral amino acid-linked PNAs was directed towards the influence of the chiral center on the helicity of PNA double helices. In all cases it was observed that the sidechain pointed away from the hydrogen-bonded nucleobases. This resulted in the formation of an "envelope" of sidechain groups around the double strand. In contrast to this in the PNAs, the piperazine oligonucleotides of the instant invention have a linkage which may be used to attach an additional side group on the same face of the rigid heterocycle as the nucleobase.

This sidechain functionality can be varied to a great extent by using D- and L-amino acids. This will allow wide modification of the properties of these nucleoside analogs. The number of possible modifications is too large to completely list, but would include, without limitation, using arginine to yield additional hydrogen bonding acceptor sites; using cysteine to give access to facile crosslinking sites; using lysine groups to compensate for electrostatic repulsion and enhance intracellular availability; using phenylalanine to induce additional hydrophobic and stacking interactions; and using histidine, which could be sufficient to obtain hydrolytic activity capable of cutting a complementary strand.

Another advantage of the piperazine-based oligonucleotide analogs of the instant invention is their ability to be used with widely available equipment. The use of PNAs in synthesis requires the availability of a dedicated and modified peptide synthesizer. A major advantage of piperazino oligonucleotide analogs in this regard will be that the oligomer synthesis may be executed on an oligonucleotide or peptide synthesizer respectively with only minor modifications. These synthesizers are generally readily available in many nucleotide laboratories.

The synthetic method used to construct the monomeric building blocks yields a high degree of side chain diversity. Specifically, EPC methods are used, starting from natural amino acids, which are transformed to diketopiperazines. After this, the diketopiperazines are reduced to piperazines. Following this, the nucleobase is attached, and this step further allows the introduction of additional R groups, as is seen in FIG. 11. In FIG. 11. "Z-AA" is used as a generic term to denote any amino acid. The amino acids used may be in either D- or L- conformation.

The availability of stable isotope-labeled amino acids will allow the creation of stable isotope-labeled piperazine analog monomers for structure evaluation by NMR. This is so since the "flexible" design of the synthetic method of the instant invention allows further modifications to be made to the heteroatoms incorporated into the monomers, as well as the synthesis of a highly diverse compound library for combinatorial structure optimization. This synthesis is highly useful since in just a few steps, it leads to DMT or MMT/ phosphoramidite monomers or chimeras with DNA ready to use on standard oligonucleotide synthesizers.

A currently used synthetic approach is a stereoselective piperazine synthesis developed by Hoechst Marion Roussell and published in the Journal of Organic Chemistry. This procedure is ideal for on resin syntheses, which allow rapid structure optimization, on resin cyclization, oligomerization, and other testing.

Following the synthetic method of the instant invention generates and characterizes activated nucleoside analogs usable in automated oligomer synthesis, as is portrayed in FIG. 9. The physicochemical and biological properties of a Gly derivative monomer were analyzed. This synthetic route was followed to construct a monomer intermediate, the proton NMR spectrum of which is contained in FIG. 8.

At this phase, tests for the activity of the phosphate-, phosphoramidate-, carboxylic acid-, and sulphonamide-monomers as substrates and inhibitors of polymerases, kinases and reverse transcriptase, can be conducted. Suitably derivatized (e.g. phosphates) may also be tested for potential antiviral activity. By varying the amino acid precursors used, it is possible to introduce additional functional and structural elements into the monomers.

The synthesis and characterization of piperazine-based oligomers and binding studies with complementary strands of natural DNA/RNA have been conducted. For this step a modified and optimized synthetic protocol on standard oligonucleotide synthesizers for piperazine oligonucleotide analogs was developed. Two-dimensional NMR methods and restrained molecular dynamics may be used to obtain the solution structures of piperazine-oligonucleotides and their hybrids with DNA and RNA. Synthesis and application of 32P-marked piperazine oligonucleotides will facilitate biological testing of these oligonucleotides towards nuclease stability and increase the analytical sensitivity range.

Chimeras of piperazine oligonucleotides with natural DNA/RNA and peptides may be synthesized, as taught in Koch et al., *Tetrahedron Lett.*, 36(38) 6933–36 (1995). This is done as part of the process of targeting sequences of medical and biomolecular relevance. Tests for bioavailability and biostability may be devised and performed including e.g. RNAse H mediated digestion of mRNA bound to piperazine-oligonucleotides; octanol-water fractioning and vesicle diffusion of fluorescence marked oligos. At this stage, combinatorial libraries for ribozyme activity within natural sequences can be synthesized and tested.

A next step involves the synthesis of chemical nucleases—the synthetic precursors of piperazine nucleotides which are homologous to EDTA and can be used to bind catalytically active metal ions. See Bigey et al., *Bioconjugate Chem.*, 8(3), 267–270 (1997), Han et al., *Biochemistry*, 33(33) 9831–44 (1994), Han & Dervan, *Proc. Natl. Acad. Sci. U.S.A.*, 91(11) 4955–59 (1994), Mack & Dervan, *Biochemistry*, 131(39) 9399–405 (1992).

The synthetic route allows access to any heteroatom substitution and combination within the rings system with or without variation of the linker length. Building a combinatorial library for DNA and RNA binding oligomers will allow the probing of the "structure space" for alternative information-encoding oligomers and allow researchers to gain insight to "why nature chose phosphates (Westheimer, *Science*, 237 (4793), 1173–78, (1987)) and pentoses (Eschenmoser, Pitsch et al., *Helv. Chim. Acta*, 76(6) 2161–83 (1993) attach. 1.)".

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed and desired to be secured by United States Letters Patent is:

1. A nucleoside analog represented by the formula:

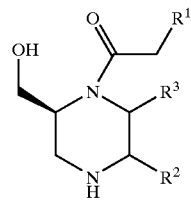

wherein $R^1$ is selected from the group consisting of adenine, thymine, uracil, guanine, cytosine, inosine, fluorouracil, allyluracil, and daunamycin, and wherein $R^2$ and $R^3$ are selected from the from the group consisting of hydrogen and all sidechains found occurring in the 20 natural amino acids, and the isomeric and diastereoisomeric forms of.

2. The nucleoside analog of claim 1, wherein $R^1$ is a nucleobase derivative selected from the group consisting of inosine, fluorouracil, and allyluracil.

3. The nucleoside analog of claim 1 wherein $R^1$ is daunamycin.

4. A compound suitably activated for solid phase synthesis and solution phase condensation to oligomers represented by the formula:

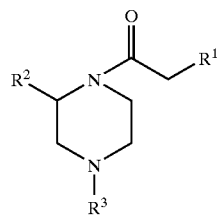

wherein $R^1$ is selected from the group consisting of adenine, thymine, cytosine, uracil, and guanine;

wherein $R^2$ is selected from the group consisting of:

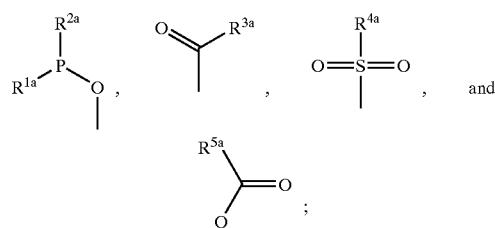

wherein $R^{1a}$ and $R^{2a}$ are selected from a group of phosphonate- and phosphoramide-protecting and activating groups consisting of hydroxyl-, cyanoethyl-, methoxy-, benzyl-, tert-butyl-, diisopropylamine-, and chloro- groups;

wherein $R^{3a}$ is selected from the group consisting of hydroxyl-, chloro-, hydroxysucciminidyl-, and pentafluorophenoxy- groups;

wherein $R^{4a}$ is selected from the group consisting of chloro-, bromo-, amido- and hydroxy- groups;

wherein $R^{5a}$ is selected from the group consisting of chloro-, hydroxy- and nitrophenyloxy- groups; and wherein $R^3$ is selected from the group consisting of MMT, DMT, Fmoc, and Boc.

5. A compound containing a number, n, of nucleoside monomers represented by the formula:

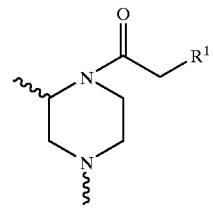

wherein $R^1$ is a nucleobase selected from the group consisting of adenine, thymine, uracil, guanine, cytosine, inosine, fluorouracil, allyluracil, and daunamycin;

wherein n is from about 1 to about 1000; and wherein the nucleoside monomers are joined by amide-, phosphonamide-, carbamate-, phosphodiester-, peptide-, or sulfonamide-bonds.

6. The compound of claim 5, wherein $R^1$ is a nucleobase derivative selected from the group consisting of inosine, fluorouracil, and allyluracil.

7. The compound of claim 5, wherein the nucleobase derivative is daunamycin.

8. The compound of claim 6, wherein n is from about 1 to about 30.

9. The compound of claim 6, wherein n is from about 30 to about 100.

10. The compound of claim 6, wherein n is from about 100 to about 1000.

11. The compound of claim 6, wherein the monomers are joined by a bond selected from the group consisting of phosphodiester and phosphonamide bonds.

12. The compound of claim 11, wherein the bond joining the monomers optionally includes a linking group which is between about 1 and about 4 carbons in length.

13. The compound of claim 6, wherein the monomers are joined by peptide bonds.

14. The compound of claim 13, wherein the peptide bonds optionally include a linking group of between about 1 and about 4 carbons in length.

15. The compound of claim 6, wherein the monomers are joined by sulfonamide bonds.

16. The compound of claim 15, wherein the sulfonamide bonds optionally include a linking group of between about 1 and about 4 carbons in length.

17. The compound of claim 6, wherein the monomers are joined by carbamate bonds.

18. The compound of claim 17, wherein the carbamate bonds optionally include a linking group of between about 1 and about 4 carbons in length.

* * * * *